United States Patent
Errico

(10) Patent No.: US 6,324,433 B1
(45) Date of Patent: Nov. 27, 2001

(54) ELECTRODE-LEAD COUPLING SKULL MOUNTED PORT ASSEMBLY

(75) Inventor: Joseph P. Errico, Far Hills, NJ (US)

(73) Assignee: ElectroCare Technologies, LLC, Summit, NJ (US)

( * ) Notice: Subject to any disclaimer, the term of this patent is extended or adjusted under 35 U.S.C. 154(b) by 0 days.

(21) Appl. No.: 09/488,997

(22) Filed: Jan. 20, 2000

(51) Int. Cl.$^7$ ....................................... A61N 1/00
(52) U.S. Cl. ............................. 607/116; 607/139
(58) Field of Search .................... 600/386, 378; 607/149, 139, 116; 604/175

(56) References Cited

U.S. PATENT DOCUMENTS

| | | | |
|---|---|---|---|
| 4,328,813 | * | 5/1982 | Ray . |
| 5,464,446 | * | 11/1995 | Dreesen et al. . |
| 5,843,150 | * | 12/1998 | Dreesen et al. . |
| 5,865,842 | * | 2/1999 | Knuth et al. . |
| 5,927,277 | * | 7/1999 | Baudino et al. . |
| 6,044,304 | * | 3/2000 | Baudino . |

* cited by examiner

Primary Examiner—Mark Bockelman
(74) Attorney, Agent, or Firm—Joseph P. Errico, Esq.; Timothy J. Bortree, Esq.

(57) ABSTRACT

An assembly for securing an electrode lead within a burr hole formed in a patient's skull and couples it to a coupling lead which extends to a remote signal generator. The securing assembly has three separate components. The first is a bone port which seats within a preformed burr hole in the skull. The bone port is a cylindrical shaped short tube with central axial hole having electrical contacts formed on the inner surface. These electrical contacts are connected to corresponding contacts in a circumferential groove formed in the upper surface of the port for receiving the proximal end of the stimulation electrode. The second component is a docking element which seats in the port. The docking element has corresponding electrical contacts on the exterior surface thereof, which connect to terminal pads in an axial bore formed therein. The coupling lead is inserted into the bore and is thereby connected to the stimulation electrode by virtue of the contacts made between the port and the docking element. A cap element seats over the port and docking elements, holding them together and securing the stimulation electrode in the assembly.

8 Claims, 5 Drawing Sheets

ELECTRODE-LEAD COUPLING SKULL MOUNTED PORT ASSEMBLY

BACKGROUND OF THE INVENTION

1. Field of the Invention

This invention relates generally to a device used in the interventional treatment of neurological disorders, and more particularly to a novel electrode-lead coupling assembly which mounts to a burr hole in a patient's skull and couples an implanted electrode to a lead which extends external to the skull to a powered signal generator.

2. Description of the Prior Art

The use of electrical stimulation of the brain for the purposes of alleviating pain and the treatment of other neurological afflictions has been utilized for a number of years, and in many instances has become the standard of care. The traditional technique comprises the implantation of a long flexible electrical lead through a burr hole in the patient's skull, and into electrical contact with the pathological section of the patient's brain. The flexible lead comprises a plurality of long helically wound wires encased in a elastomeric sheath. The distal end of the wire lead include electrical contacts and are placed in the brain. Once positioned, the lead is secured to the skull such that the internal portion is locked, and prevented from movements. The proximal end of the wire lead remain external to the skull, and is coupled to an extension connector which joins the electrical wires to an electrical generator.

As is clear from the delicacy of the surgical field, it is critical to utilize robust instruments and implants which are not easily broken, and which do not lend themselves easily to unwanted movements. In particular, there are two concerns which the surgeon has when utilizing traditional equipment. The first concern is related to the securing of the lead to the skull. More particularly, when an electrode lead is implanted, the position of the active tip is critical. The effects of the field generated by the electrical contacts is highly position dependent, and as a result, movement of the electrode after proper positioning can reduce or eliminate all effectiveness of the treatment. As it can be a very tedious process to find the appropriate location within the brain for the active tip, it is also critical that once the lead is situated, it should not be moved accidentally. If external portions of the lead are not secured, subsequent manipulations of the electrode leads can cause this unwanted movement.

One such device which is presently available in the art is illustrated in FIG. 1, and is described in U.S. Pat. No. 5,464,446. It comprises a first port member 22 which is cylindrical and seats in the burr hole formed in the patient's skull 24. The exterior lateral surface of the port includes a contoured circumferential flange portion 26 which is intended to form a seal with the inner lateral surface 28 of the burr hole. The upper portion of the port member includes an outwardly extending rim 30 which seats against the exterior surface of the skull 30 around the edge of the burr hole when the port is inserted fully in the burr hole. This upper contour is also designed to mate with a cap section 32. The central axis of the seating member 22 forms a channel through which the electrode 34 seats and can slide prior to being locked in place. The cap 32 has a pair of channels formed therein; a first 36 which extends axially along the same direction as the axial passage in the port member, and the second 38 which extends out radially along the undersurface. The cap 32 engages the upper contour (and requires a suture 40 to hold the members together) in such a way that the electrode lead is compressed and is thereby locked in place. The use of a suture to secure the electrode, even indirectly, is a considerable drawback as it is difficult to manipulate, not easily reversible, and does not provide a readily obvious means for ensuring that the lead is truly secured against movements when the external portion is manipulated during the remainder of the surgery. Also, the compression lock, as in the first example is not easily viewed as it happens under the cap member.

In co-pending application, U.S. Ser. No. 09/489,000, entitled "A Skull Mounted Electrode Lead Securing Assembly", assigned to the same assignee as the present invention, the present inventors have provided an invention which is an advance over the prior art in the field of securing the electrode lead to the skull. The specification of said application is hereby included fully, by reference.

The second concern which surgeons have regarding the presently available equipment is with regards to the electrical joining of the proximal end of the electrode lead to the extending cable which couples the electrode to the remote electrical signal generator. Unfortunately, because of the techniques and equipment used in implantation of the lead within the brain, the joining of the proximal end of the electrode to the extending cable occurs after the distal end of the electrode has been fully implanted and positioned, and the cannula has been removed. At this stage, damage to the proximal end of the electrode, even if such damage does not cause the distal end to move, will require the removal of the implanted lead. Removal of the lead requires that the entire implantation procedure to be repeated (a process which can take several hours). The presently available extension cables and the coupling means for connecting the proximal end of the lead thereto are prone to causing damage to the proximal end of the implanted electrode.

One alternative solution to this concern is to provide a more robust coupling end to the implanted lead. This alternative requires several modifications of equipment used during the implantation steps. The present inventors have provided for several such modifications, including co-pending applications U.S. Ser. Nos. 09/489,004, 09/489,003 and 09/489,002 entitled "A Helically Slotted Cannula", "An Axially Separable Cannula", "A Coupling Mechanism for Connecting A Deep Brain Stimulation Lead to an Electrical Extension Cable", respectively, each of which is assigned to the assignees of the present invention, the specifications of each being incorporated herein, fully, by reference.

The solution of the present invention is related, instead, to providing a more reliable coupling for the electrode which reduces the potential for damage and simultaneously prevents the implanted portion of the electrode from being moved once properly positioned.

The objects of the present invention are, therefore, clearly to provide an electrode securing assembly which reliably, easily, reversibly, and obviously locks an electrode lead to the skull, and most importantly, prevents the unwanted movement of the implanted portion of a deep brain stimulation lead during the manipulation of the external portion after the active internal tip has been properly positioned.

Simultaneously, it is an object of the present invention to provide an assembly which reliably and non-destructively couples the implanted electrode lead to the extension lead.

In addition, it is also an object of the present invention to provide a mechanism which is easily manipulated by the surgeon under the conditions of the surgical field.

SUMMARY OF THE INVENTION

The preceeding objects of the present invention are provided by a device which comprises a first cylindrical port member which seats into a burr hole in the skull, said cylindrical port member including an axial electrode receiving channel disposed on the inner surface of the cylinder, a circumferential electrode receiving channel formed in the upper end of the cylinder, and a series of electrical contact splines formed on the inner surface of the cylinder. The circumferential channel formed in the upper surface of the cylinder includes a series of spaced apart electrical contact pads which are aligned with the electrical contacts of the proximal end of a deep brain stimulation lead. The electrical contact splines are electrically connected to the contact pads on the inner surface of the circumferential electrode receiving channel.

The present invention further includes a cylindrical docking member which seats in the cylindrical opening of the port member. The docking member includes an axial recess formed in the side thereof which may be aligned with the axial electrode receiving channel of the port member and by proximity association with the port member, hold an electrode lead securely in place therebetween. The cylindrical docking member further includes a corresponding number of axial splines formed in the sidewall thereof which mate with the splines of the port member. A deep axial recess is also formed in the upper portion of the docking member. This recess is designed to receive the distal tip of the electrical coupling cable which couples the deep brain stimulation lead to the signal generator. The recess, therefore, includes a series of electrical conduits individually connecting the splines to electrical contacts on the inner surface of the recess.

The present invention further includes a cap member which seats and engages the upper portion of the first cylindrical port member. The cap member includes a through hole which is slightly narrower than the axial opening in the port member, and narrower than the docking member. Placement of the cap on the upper portion of the port member, therefore, once the docking member is inserted into the opening, secures the docking member in the port. The undersurface of the cap includes a circumferential groove which corresponds to the circumferential recess in the upper surface of the port member. When fully assembled, the proximal tip of the deep brain stimulation lead is placed in the circumferential recess of the port member, and the cap is engaged thereon. Together, the port member and the cap securely retain the proximal end of the deep brain stimulation.

In brief, the implantation surgery is carried out, using this assembly, as follows. The patient's is prepared by exposing the skull and opening a burr hole therein. The port member is inserted into the burr hole. A cannula including a deep brain stimulation electrode lead (which may also include a microelectrode recording mechanism as disclosed in co-pending U.S. patent application, U.S. Ser. No. 09/489,001, entitled "A Device for Performing Microelectrode Recordings Through the Central channel of a Deep-Brain Stimulation Electrode", assigned to the same assignee as the present invention, the disclosure of which is hereby includes fully by reference), is inserted into the patient's brain, and manipulated into proper position. The cannula is then removed and the exposed portion of the lead is then pressed into the lateral channel formed in the side wall of the port member. The docking member is then inserted into the opening in the port, in such a way as to maintain the lead in the channel and secure it there. The proximal tip of the electrode is then inserted into the circumferential recess in the upper portion of the port member such that the electrical contacts of electrode are in electrical communication with the splines on the inner surface of the port opening, and by association of the port and docking members, to the inner electrical contacts in the axial recess formed in the docking member. The cap is then placed on top of the port, thereby securing the proximal tip of the electrode in the circumferential recess, and the docking member in the opening. The distal end of the extension cable is then inserted and secured in the axial recess formed in the docking member, such that the implanted electrode lead is connected to the remote signal generator. Once complete, this assembly successfully secures the implanted portion of the electrode from any possible motion, connects the proximal contact pads of the implanted electrode to the extension cable without risk of damage to the implanted electrode, and is sufficiently easy to manipulate that it is not difficult for the surgeon to use in the surgical field.

Additional advantages of the present invention shall be readily understandable from the detailed description of certain preferred embodiments described more completely in the following sections, and with reference to the accompanying figures.

A BRIEF DESCRIPTION OF THE DRAWINGS

THE DETAILED DESCRIPTION OF THE PREFERRED EMBODIMENTS

While the present invention will be described more fully hereinafter with reference to the accompanying drawings, in which particular embodiments are shown, and with respect to methods of implantation, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
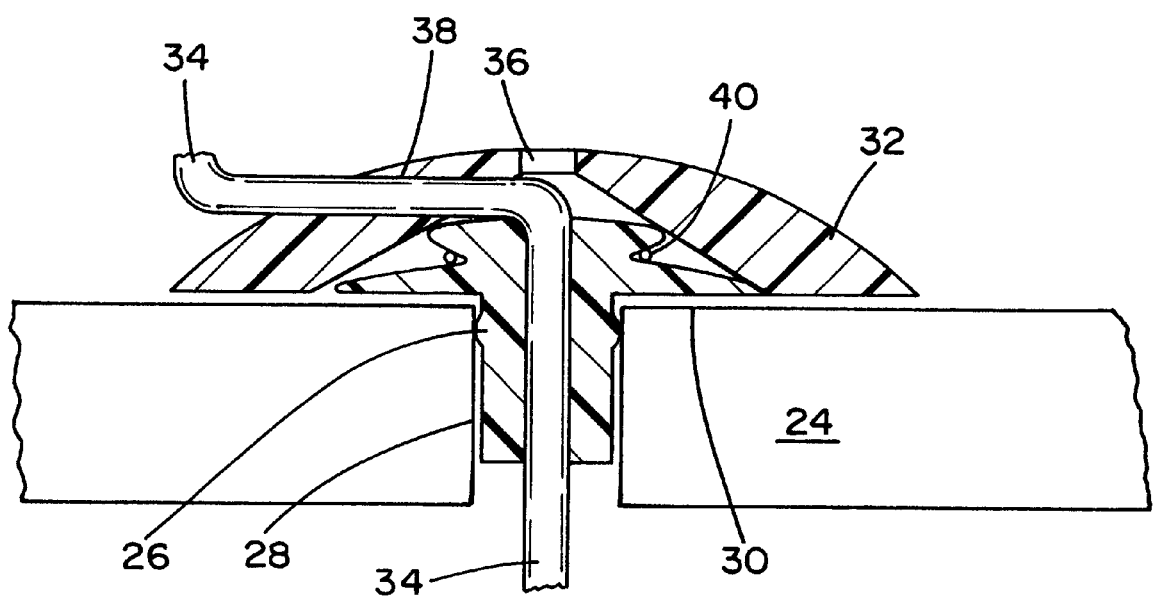
FIG. 1 shows a side perspective view of another electrode securing device of the prior art which couples to the skull.
Figure 2:
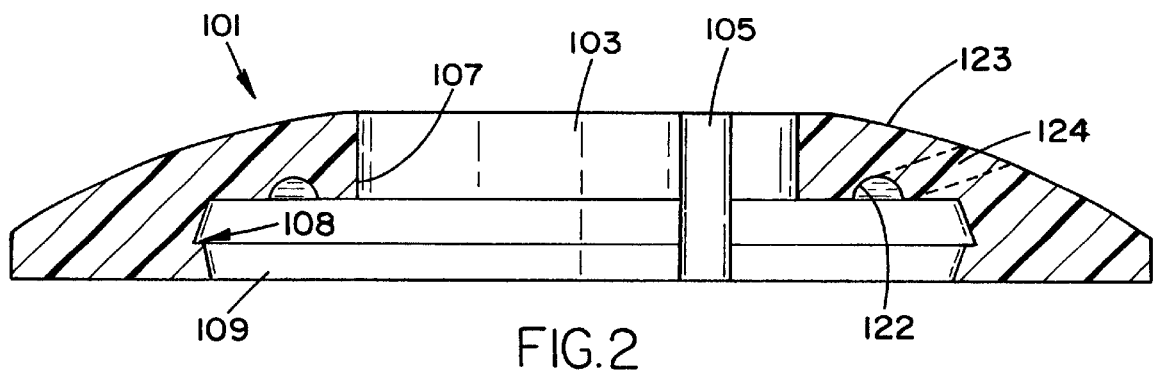
FIG. 2 shows a side cross-section of the burr hole cap which is an aspect of the present invention.
Figure 3:
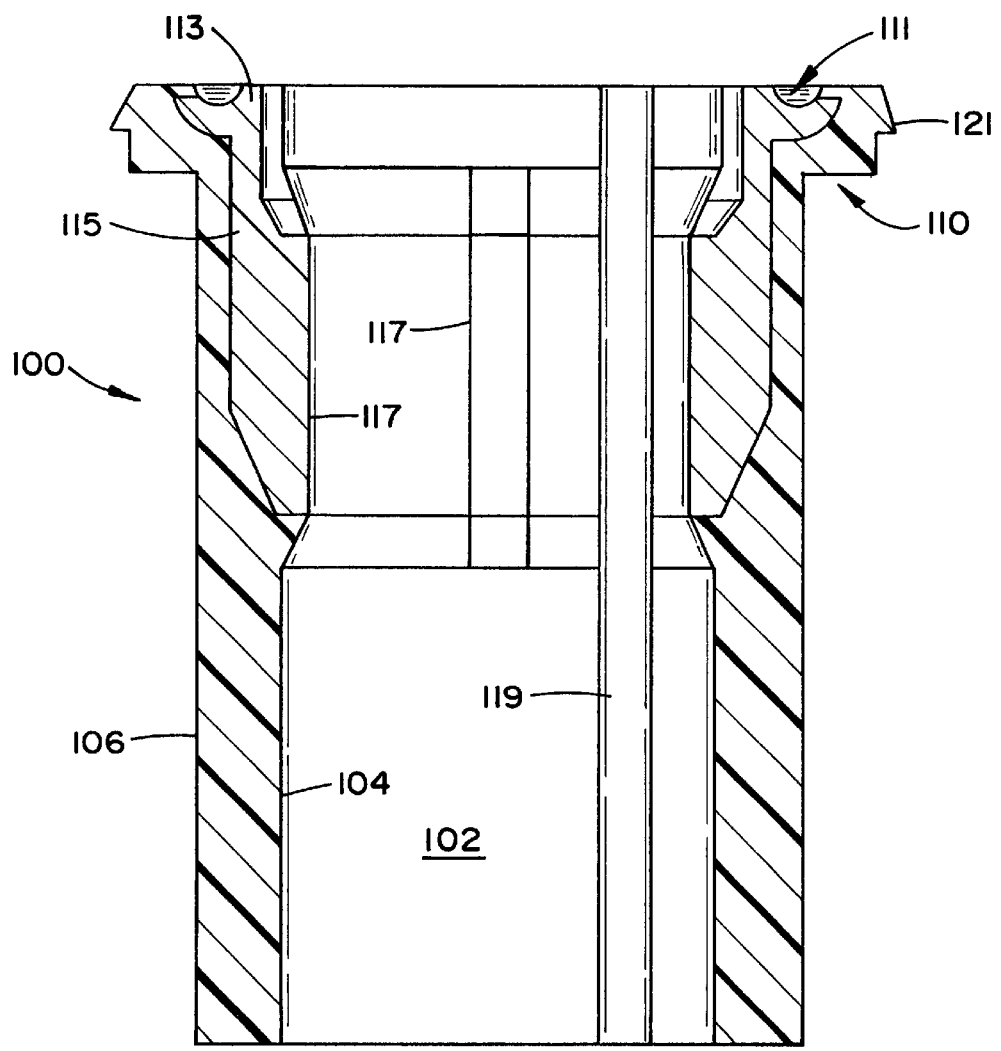
FIG. 3 shows a cross-section view of a burr hole port which is an aspect of the present invention.

Referring now to FIGS. 2 and 3, the present invention comprises a cylindrical skull port member 100 which is designed to securely fit within the burr hole formed in a patient's skull, through which the surgeon implants the active tip of the electrode lead, and a cap member 101 which seats on the upper portion of the port member 100. More particularly with respect to the port member, the member 100 includes a central opening 102 and a round sidewall 104. The exterior surface 106 of the sidewall 104 may include at least one circumferential rib (not shown), and preferably multiple ribs. These ribs, when provided, are preferably made of an elastomeric material (for example silicone). The ribs are provided for enhanced gripping and holding of the inner surface of the burr hole in the skull. Other than these ribs, the exterior surface of the cylindrical port is largely smooth, having only a laterally extending lip 110 at the upper end. This lip 110 is provided so that as the port 100 is inserted into the burr hole, the lip 110 seats against the upper surface of the skull and prevents the port 100 from passing too deeply into the brain case.

The upper lip 110 further includes a circumferential recess 111 formed in the upper annular, surface of the port member 100. This circumferential recess 111 forms an annular groove which is designed to receive the proximal tip of an implanted deep brain stimulation electrode. Along this annular groove are a plurality of spaced apart and electrically insulated electrical contact pads 113. These electrical contact pads 113 are provided in approximate correspondence with the spaced apart disposition of the contact pads of the proximal tip of the deep brain stimulation electrode. The electrical contact pads 113 of the port member 100 are connected, via electrical conduits 115, for example wires, located within the sidewall of the port member, terminating in electrical contacts 117 formed on the inner surface 104 of the cylindrical opening 102.

More particularly, with respect to the interior surface 104 of the port's central opening, the electrical contacts 117, which are connected to the contact pads 113 of the annular groove 111, are provided as spaced apart axial splines 117. These splines are designed to engage electrical contact grooves formed on a docking member (see below with respect to FIG. 5) and extend for a limited distance along the inner surface 104 of the port member 100. In addition to the electrical contact splines 117, the inner surface 104 of the port member 100 also includes an axial channel 119 which is designed to receive therein the deep brain stimulation lead. More specifically, the deep brain stimulation lead is implanted into the patient's brain such that a portion remains external to the brain and extends out through the burr hole. The portion of the deep brain stimulation electrode which traverses the burr hole (and, therefore, through the opening 102 in the port member 100) seats in the channel 119.

Referring again to the lip 110 of the port member 100, the lip 110 includes a circumferential latch mechanism 121, which comprises a sloped extending ledge which is designed to engage a similar conformation on the cap member 101, which is described hereinbelow, with reference to FIG. 2. The cap member 101 comprises a disk shape, having a central opening 103. The upper portion 107 of the opening 103 is narrower in diameter than the opening 102 in the port member 100. This difference in diameters permits the cap member 102 to act as a retaining means for any docking member (see discussion of docking member with respect to FIG. 5) which may be inserted into the opening 102 in the port member 100. In addition, the cap member 101 has a radial carved out groove 105 which corresponds to, and aligns with, the axial channel 119 formed in the sidewall 104 of the port member 100. The groove 105 receives the deep brain stimulation electrode therethrough as well.

The lower portion 109 of the opening 103 in the cap 101 is approximately the same diameter as the lip 110 of the port member 100. The inner surface 108 of the lower portion 109 of the opening 103 includes a conformation which is designed to engage, deflect, and then to seat against the latch ledge 121 of the lip 110 of the port member 100. This engagement permits the cap 101 to simply, easily, and securely grip the upper portion of the port member 100 simply by being pressed onto the upper portion of the port 100.

Disposed at an intermediate radial location along the interface between the upper 107 and lower 109 portions of the opening 103 in the cap 101, is a circumferential groove 122. This groove is designed to mate with the corresponding groove 111 in the upper surface of the port member 100. More particularly, grooves 111 and 122 together form a toroidal shaped volume into which the proximal tip of the deep brain stimulation electrode is secured. It is secured therein by virtue of the fact that the diameter of the toroidal passage is slightly more narrow than the uncompressed electrode tip. The electrode tip, however, is comprised of an elastomeric material and can deflect slightly. This compression serves to both secure the electrode in the toroidal passage, and to ensure that the contact pads 113 of the port member 100 are in electrical contact with the contacts of the proximal tip of the electrode.

The upper surface 123 of the cap may include a hole 124 through which the exterior portion of the deep brain stimulation electrode, which passes out from the central opening 103 in the cap 101, may be inserted into the groove 111 of the port member. Alternatively, the cap 101 and the port member 100 may each include a radial carve out (not shown) for permitting the deep brain stimulation electrode access to the groove 111.

Figure 4:
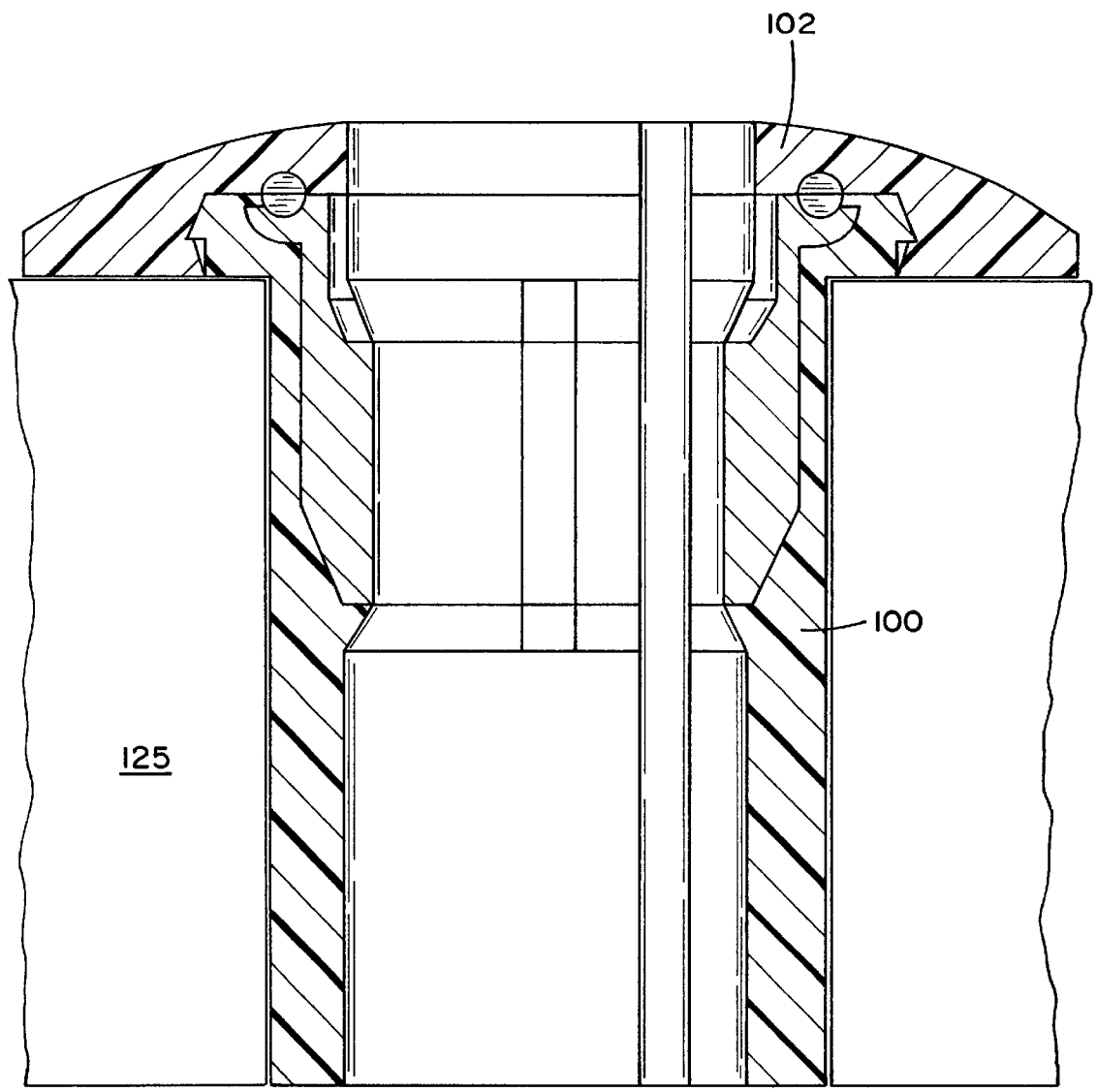
FIG. 4 shows a side cross section of the port and cap initially shown in FIGS. 2 and 3 in their engaged disposition.

Referring now to FIG. 4, the coupling of the port and cap members together within the burr hole of a skull 125 is shown in a side cross section view.

Figure 5:
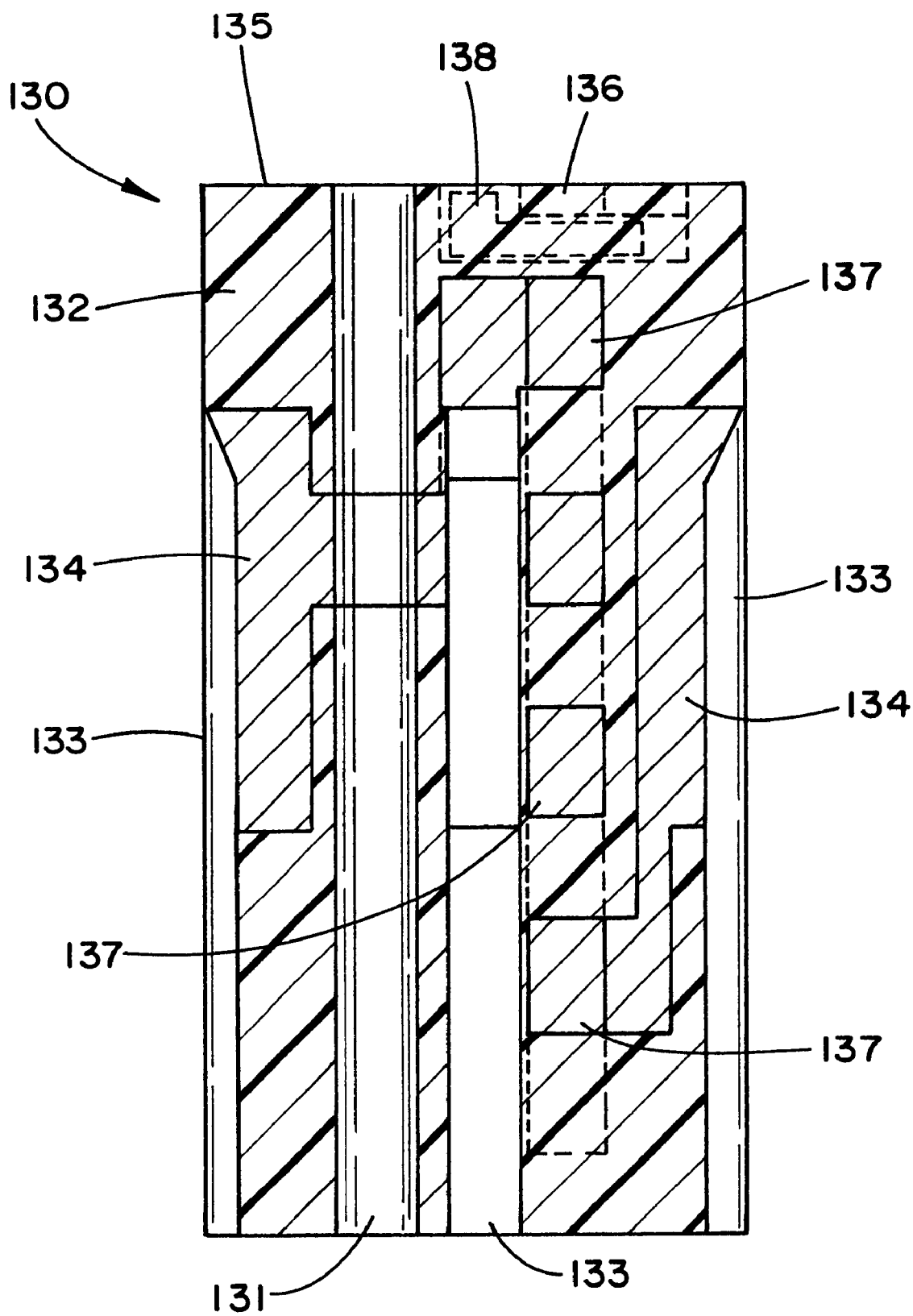
FIG. 5 shows a side cross section view of the docking member which is an aspect of the present invention.

Referring now to FIG. 5, the docking member 130 of the present invention is shown in a side view, wherein important internal features are shown in phantom. The docking element 130 is designed to slide into and seat in the opening 102 of the port member 100. The docking member 130 comprises a cylindrical body 132 having an axial groove 131 extending along the exterior surface of the cylinder. The axial groove 131 corresponds with the groove 119 formed in the sidewall 104 of the port member 100 for retaining the portion of the deep brain stimulation electrode with passes therethrough. As with the corresponding circumferential grooves 111 and 122 of the cap 101 and the port 100, the axial channels 119 and 131 of the port 100 and docking member 130, respectively, are designed to secure the electrode disposed therein by virtue of a slight interference between the uncompressed diameter of the electrode and the effective diameter of channel 119 and 131 between the joined elements 100 and 130. As introduced above, the elastomeric material of the deep brain stimulation electrode makes this compression interference retention possible.

The docking element 130 further includes a plurality of axial spline grooves 133 which extend partially up the exterior surface of the member 130. These axial spline grooves 133 correspond to the axial splines 117 of the opening 102 in the port member 100. These splines 133 terminate at a position lower than the top of the docking member 130, such that the docking member 130 is prevented from descending into the port member 100 beyond a fully engaged disposition.

The upper portion of each of the axial splines 133 includes an electrical contact 134. Each electrical contact 134 independently extends into the center of the docking member 130. Within the center of the docking element 130, and extending down from the upper surface 135 thereof, is a bore 136. This bore 136 is designed to receive the distal tip of the coupling cable which joins the signal generator to the deep brain stimulation electrode. More particularly, the distal tip of the coupling cable includes a plurality of electrical terminals. These terminals seat in the bore against corresponding contacts surfaces 137 in the bore. These contact surfaces 137 are the ones coupled independently to the contacts 134 at each axial spline 133. Thus, when the distal end of the coupling lead is inserted into the axial bore 136 o the docking member 130, each of the splines 133 is connected to an individual wire within the coupling lead, and may, thereby, be independently biased with an electrical signal from the signal generator. Correspondingly, when the docking member 130 is properly disposed in the port member 100 with the proximal tip of the deep brain stimulation electrode properly positioned in the circumferential groove 111 of the port 100, the individual electrical contacts at the distal tip of the electrode are biased separately and independently.

In addition to the foregoing, the upper surface of the docking member 130 also includes a locking mechanism 138 which may be utilized to secure the distal tip of the coupling lead in the axial bore 136. A more complete description of the locking mechanism which may be utilized in this embodiment, see co-pending U.S. patent application U.S. Ser. No. 09/489,000, entitled "A Skull Mounted Electrode Lead Securing Assembly" which was introduced above.

Figure 6:
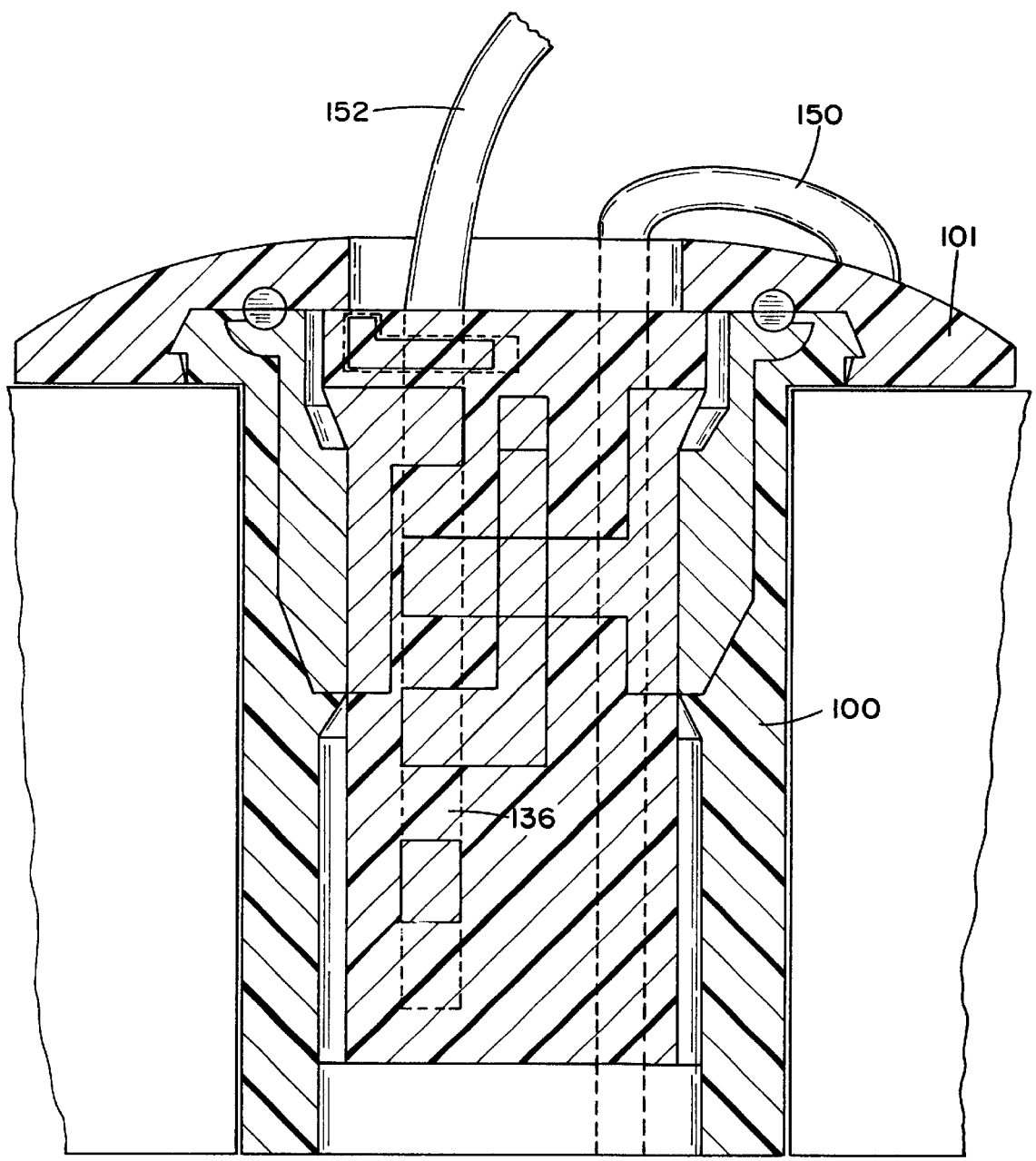
FIG. 6 shows a side cross section view of the docking member mounted in the port member, with the cap member seated in its securing position, wherein an implanted electrode and an electrode connecting cable are each securely held in the assembly.

Referring now to FIG. 6, a description of the assembly of the present invention, in accordance with the principles of its use, during an implantation surgery is herein provided. First, the patient's head is prepared by exposing the skull and opening a burr hole therein. The burr hole diameter used in such surgeries is generally in the range of 14 to 16 millimeters. The port member 100 is inserted into the burr hole. A cannula including a deep brain stimulation electrode lead 150 (which may also include a microelectrode recording mechanism as disclosed in co-pending U.S. patent application, U.S. Ser. No. 09/489,001, entitled "A Device for Performing Microelectrode Recordings Through the Central channel of a Deep-Brain Stimulation Electrode", assigned to the same assignee as the present invention, the disclosure of which is hereby includes fully by reference), is inserted into the patient's brain, and manipulated into proper position. The cannula is then removed. The portion of the electrode 150 which is traversing the hole is then pressed into the channel 119 in the side wall 104 of the port member 100. The docking member 130 is then inserted into the opening 102 in the port 100, in such a way as to maintain the electrode in between the channel 119 of the port and the channel 131 of the docking member 130. In addition, the splines 117 of the port member 100 should be aligned with the splines 133 of the docking member 130 such that electrical contact is made between the respective contact surfaces 134 and 117.

The proximal tip of the electrode is then inserted into the circumferential groove 111 in the upper portion of the port member 100 such that the electrical contacts of electrode are seated next to electrical contacts 113 in the port member. The cap 101 is then seated on the port member 100, and secured in place by the ratcheted latching association with the inner surface 108 of the lower portion 109 of the cap opening 103 and the exterior lateral surface 121 of the lip 110 of the port 100. The placement of the cap 101 secures the proximal tip of the electrode in the circumferential groove 111 and most importantly, the terminals of the electrode against the contact pads 113 of the groove.

The distal tip of the lead 152 which couples the signal generator (not shown) to the deep brain stimulation electrode 150 is then inserted into the bore 136 of the docking member 130. By inserting this tip into the bore, and fully seating it therein, the electrical communication of the signal generator's individual signals to the individual terminals at the distal end of the deep brain stimulation electrode is complete. The coupling lead is then locked in the docking member by means of a latching mechanism 138. Once complete, this assembly successfully secures the implanted portion of the electrode from any possible motion, connects the proximal contact pads of the implanted electrode to the extension cable without risk of damage to the implanted electrode, and is sufficiently easy to manipulate that it is not difficult for the surgeon to use in the surgical field.

While there has been described and illustrated specific embodiments of new and novel skull mounted electrode lead securing and coupling assembly for reliably and securely fixing an implanted electrode lead to the skull and coupling it reliably and safely to a remote signal generator, it will be apparent to those skilled in the art that variations and modifications are possible without deviating from the broad spirit and principle of the present invention which shall be limited solely by the scope of the claims appended hereto.

We claim:
1. An electrode securing and electrical coupling assembly for securing a deep brain electrode lead to a skull of a patient and coupling said lead to a remote signal generator via a coupling lead; comprising:
   a cap element having an axial opening formed therein;
   a cylindrical port element for seating in a hole formed in said skull of said patient, said port element including and upper end and a lower end, said port element further including
      a central opening providing communication between an interior of said skull and an exterior of said skull, said opening being wider than the opening in said cap element,
      an annular lip formed at the upper end, said annular lip including a circumferential groove for receiving therein an end of a deep brain stimulation electrode having at least one electrical terminal, said circumferential groove including at least one electrical terminal pad corresponding to at least one electrical terminal of said electrode,
      an axial recess formed in a sidewall of said opening for securing said electrode therein,
      at least one spline, said at least one spline having at least one individual contact pad, each contact pad being individually electrically connected via conduits in the sidewall of said port to said electrical terminal pads in said circumferential groove, and
      means on said lip for coupling to said cap element; and
   a docking element having
      at least one axial recess formed in the top thereof for receiving therein an end of said coupling lead, said recess including at least one electrical contact surface for engaging terminals formed on said tip of said coupling lead,
      at least one spline corresponding to and when fully assembled in electrical contact with the at least one spline of said port element, said at least one electrical contact surface of said recess in said docking element being in individually electrical communication with the at least spline said docking element, such that the coupling lead is in electrical communication with said deep brain stimulation electrode,
      means for securing said coupling lead in said recess in said docking element.
2. The electrode securing assembly as set forth in claim 1, wherein said cap element and said lip of said port element include an engaging ratchet and latch mechanism whereby said cap seats securely in said port element.

3. The electrode securing assembly as set forth in claim 1, wherein said cap element includes a circumferential groove formed on an undersurface thereof, said circumferential groove corresponding to the circumferential groove in said lip portion of said port element, the association of which when the cap is placed on the port element causes the tip of the deep brain stimulation electrode to be secured in said groove.

4. The electrode securing assembly as set forth in claim 1, wherein said docking element includes an axial groove which corresponds to the axial recess formed in the sidewall of the port element such that the association of the docking element and the port element serves to lock the deep brain stimulation electrode therein.

5. The electrode securing assembly as set forth in claim 1, wherein said at least one electrical terminal on said deep brain stimulation electrode comprises four spaced apart terminals and said at least one electrical terminal pad in said circumferential groove in said port member comprises a plurality of terminal pads, each being correspondingly electrically spaced from one another.

6. The electrode securing assembly as set forth in claim 5, wherein said at least one spline on said port member and said at least one corresponding spline on said docking member each comprise a single spline, each spline including four corresponding spaced apart contact pads which align with one another when the docking element is fully inserted into the port element.

7. The electrode securing assembly as set forth in claim 5, wherein said at least one spline on said port member and said at least one corresponding spline on said docking member each comprises four splines, each of which includes a single contact pad, corresponding pairs of which align with one another when the docking element is fully inserted into the port element.

8. The electrode securing assembly as set forth in claim 1, wherein said at least one terminal surface in said axial recess in said docking element comprises a plurality of terminal surfaces corresponding to the number of terminals on said coupling lead.

* * * * *